(12) United States Patent
Yamada et al.

(10) Patent No.: US 11,779,593 B2
(45) Date of Patent: *Oct. 10, 2023

(54) AGENT FOR IMPROVING OCULAR SUBJECTIVE SYMPTOMS AND METHOD THEREOF

(71) Applicant: SEIKAGAKU CORPORATION, Tokyo (JP)

(72) Inventors: Masamichi Yamada, Tokyo (JP); Chiyo Sakenaga, Tokyo (JP); Keiichiro Arai, Tokyo (JP); Kazutaka Yamamoto, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 53 days.

This patent is subject to a terminal disclaimer.

(21) Appl. No.: 17/509,576

(22) Filed: Oct. 25, 2021

(65) Prior Publication Data

US 2022/0105125 A1 Apr. 7, 2022

Related U.S. Application Data

(63) Continuation of application No. 16/922,452, filed on Jul. 7, 2020, now Pat. No. 11,185,558, which is a continuation of application No. 15/539,771, filed as application No. PCT/JP2015/086233 on Dec. 25, 2015, now abandoned.

(30) Foreign Application Priority Data

Dec. 26, 2014 (JP) ................................ 2014-263710

(51) Int. Cl.
*A61K 31/728* (2006.01)
*A61K 9/08* (2006.01)
*A61P 27/04* (2006.01)
*A61P 27/02* (2006.01)
*A61K 9/00* (2006.01)

(52) U.S. Cl.
CPC .......... *A61K 31/728* (2013.01); *A61K 9/0048* (2013.01); *A61K 9/08* (2013.01); *A61P 27/02* (2018.01); *A61P 27/04* (2018.01)

(58) Field of Classification Search
None
See application file for complete search history.

(56) References Cited

U.S. PATENT DOCUMENTS

| | | |
|---|---|---|
| 5,770,628 A | 6/1998 | Cantoro |
| 5,789,462 A | 8/1998 | Motani et al. |
| 6,025,444 A | 2/2000 | Waki et al. |
| 8,758,819 B2 | 6/2014 | Asculai |
| 8,969,319 B2 | 3/2015 | Miyamoto et al. |
| 2008/0306022 A1 | 12/2008 | Miyamoto et al. |
| 2010/0292156 A1 | 11/2010 | Maggi |
| 2011/0195927 A1 | 8/2011 | Xia |
| 2011/0207695 A1 | 8/2011 | Miyamoto et al. |
| 2015/0196574 A1 | 7/2015 | Miyamoto et al. |

FOREIGN PATENT DOCUMENTS

| | | |
|---|---|---|
| EP | 1217008 A1 | 6/2002 |
| JP | H09-87236 | 3/1997 |
| JP | H09-136902 A | 5/1997 |
| JP | 2009-511423 A | 3/2009 |
| WO | 2008/126803 A1 | 10/2008 |

OTHER PUBLICATIONS

C. Fenga, et al., American Journal of Ophthamology, vol. 158, pp. 41-48 (2014).
F. A. Adatia et al., Canadian Journal of Ophthamology, vol. 39, pp. 767-771 (2004).
"Stability Testing of New Drug Substances and Products Q1A(R2)", ICH Harmonised Tripartite Guideline (2003).
K. K. Nichols, "Patient-Reported Symptoms in Dry Dye Disease", The Ocular Surface, Jul. 2006, vol. 4, No. 3, pp. 137-145 (9 pages).
Extended European Search Report issued in European Application No. 15873273.5, dated Jul. 24, 2018 (9 pages).
International Search Report issued in PCT/JP2015/086233 dated Mar. 8, 2016 (2 pages).
Written Opinion of the International Searching Authority issued in PCT/JP2015/086233 dated Mar. 8, 2016 (3 pages).
Chinese Office Action dated Dec. 6, 2019 in Chinese Patent Application No. 201580070446.4 (with machine translation).
Package insert of Hyalein ophthalmic solution [Effects] (2018) with partial English translation.
Rosenthal et al., The Ocular Surface, Jan. 2009, vol. 7, No. 1, p. 28-40.
Fenga et al., American Journal of Ophthalmology, 158(1), Jul. 2014, p. 41-48.
Adatia et al., Canadian Journal of Ophthalmology, 39(7), 2004, p. 767-771.
Japanese definition of dry eye and revision of diagnostic criteria (2016) with a partial English translation.
Sullivan et al., Acta Ophthalmologica, vol. 92 Issue 2, p. 161-166 (2014).
Notice of Reasons for Refusal dated Jan. 14, 2020 in Japanese Patent Application No. 2016-566512 (with English language translation), 10 pages.
Decision of Refusal dated Oct. 13, 2020 in Japanese Patent Application No. 2016-566512 (with English language translation), 7 pages.
Riger Vogel, et al, "Demonstration of Efficacy in the Treatment of Dry Eye Disease with 0.18% Sodium Hyaluronate Ophthalmic Solution (Vismed, Rejena)," American Journal of Ophthalmology, vol. 149, No. 4, Apr. 2010, pp. 594-601.
Package insert for Hylein(R) sodium hyaluronate ophthalmic solution. (Year: 1995).
Partial translation of package insert for Hylein(R) sodium hyaluronate ophthalmic solution. (Year: 1995).

(Continued)

*Primary Examiner* — Leigh C Maier
(74) *Attorney, Agent, or Firm* — Oblon, McClelland, Maier & Neustadt, L.L.P.

(57) ABSTRACT

Provided is an agent for improving human ocular subjective symptoms containing hyaluronic acid having an aminoalkyl cinnamate covalently bonded thereto.

8 Claims, 5 Drawing Sheets

(56) References Cited

OTHER PUBLICATIONS

Fenga, C. et al "Comparison of ocular surface disease index . . . " Am. J. Ophthalmol., vol. 148, pp. 41-48. (Year: 2014).
Sullivan, B. et al "Correlations between commonly used objective signs and symptoms . . . "Acta Ophthalmol., vol. 92, pp. 161-166. (Year: 2014).
Adatia, F. et al "Correlations between corneal sensitivity . . . " Can. J. Ophthalmol. vol. 39, pp. 767-671. (Year: 2004).
Rosenthal, P. et al "Corneal pain without stain . . . " the Ocular Science, vol. 7, No. 1, pp. 28-40. (Year: 2009).

AGENT FOR IMPROVING OCULAR SUBJECTIVE SYMPTOMS AND METHOD THEREOF

CROSS REFERENCE TO RELATED APPLICATIONS

This application is a continuation of U.S. patent application Ser. No. 16/922,452, filed on Jul. 7, 2020, which was a continuation of U.S. patent application Ser. No. 15/539,771, filed on Jun. 26, 2017, which was a 371 of International Patent Application No. PCT/JP2015/086233, filed on Dec. 25, 2015, and claims priority to Japanese Patent Application No. 2014-263710, filed on Dec. 26, 2014.

TECHNICAL FIELD

The present invention relates to an agent for improving human ocular subjective symptoms and method thereof.

BACKGROUND ART

Improvement of ophthalmic abnormalities has conventionally been assessed focusing primarily on external observation and evaluation (objective sign), while little emphasis has been placed on evaluation from the subjective viewpoint of the patient in the manner of ophthalmic discomfort or distress (subjective symptoms). For example, the ameliorative effects of dry eye, one of the ophthalmic abnormalities, have come to be evaluated by focusing primarily on objective sign such as normalization of tear fluid volume or decreases in the damaged areas of corneal and conjunctival epithelia. In actuality, although sodium hyaluronate, diquafosol sodium and rebamipide in Japan, and cyclosporine in the U.S., have been approved for use as ophthalmic solutions prescribed for dry eye, ophthalmic solutions have yet to be approved that satisfy the requirements of improving subjective symptoms in addition to improving objective sign.

Although hyaluronic acid having a hydrophobic residue bound thereto is known to be effective against ophthalmic abnormalities such as dry eye (see, for example, Patent Document 1), the efficacy thereof is essentially based entirely on "objective sign" as described above, and it has yet to be evaluated from the viewpoints of improvement and/or treatment of subjective symptoms.

PRIOR ART DOCUMENTS

Patent Documents

Patent Document 1: JP-T 2009-511423

DISCLOSURE OF THE INVENTION

Problems to be Solved by the Invention

Objective sign and subjective symptoms do not necessarily indicate similar tendencies, and subjective symptoms may be poor while objective sign are favorable, or conversely, objective sign may be poor while subjective symptoms are favorable. In addition, existing ophthalmic solutions prescribed for dry eye require the patient to administer the ophthalmic solution over a long period of time until the efficacy thereof is demonstrated, resulting in the problem of patients with serious symptoms of dry eye losing the will and desire to continue to patiently administer the same ophthalmic solution over a long period of time, and thereby creating a desire for the providing of a drug capable of demonstrating its effect immediately after the start of administration.

An object of the present invention is to provide an agent and method for improving human ocular subjective symptoms and method thereof.

Means for Solving the Problems

As a result of conducting extensive studies to solve the aforementioned problems, the inventors of the present invention found that a compound in which an aminoalkyl cinnamate is covalently bonded to hyaluronic acid (hereinafter referred to as "HA") demonstrates the effect of improving subjective symptoms of the eyes in humans, thereby leading to completion of the present invention.

Namely, the present invention provides an agent for improving human ocular subjective symptoms (hereinafter referred to as the "pharmaceutical preparation of the present invention") containing HA having an aminoalkyl cinnamate covalently bonded thereto. This preparation is in the form of a solution and the HA having an aminoalkyl cinnamate covalently bonded thereto is preferably contained at a concentration of 0.3% (w/v). In addition, the human to whom this preparation is administered is preferably a person with dry eye.

In addition, the present invention provides a method for improving human ocular subjective symptoms that comprises a step for administering HA having an aminopropyl cinnamate covalently bonded thereto to a human eye (hereinafter referred to as the "method of the present invention"). This HA having an aminopropyl cinnamate covalently bonded thereto is preferably administered in the form of a solution having a concentration of 0.3% (w/v). In addition, the human to whom this solution is administered is preferably a person with dry eye.

Effects of the Invention

According to the present invention, an HA-based preparation for improving human ocular subjective symptoms and a method for improving human ocular subjective symptoms using that HA-based compound are provided.

MODE FOR CARRYING OUT THE INVENTION

Figure 1:
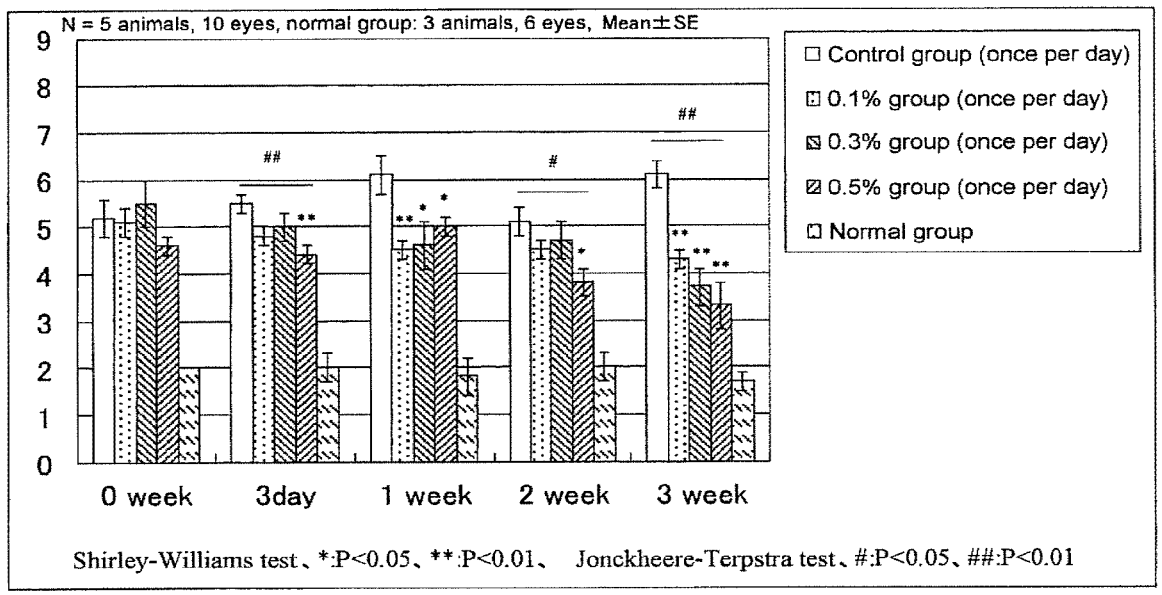
FIG. 1 indicates the degree of fluorescein staining in the case of having administered a preparation to the eye of a model animal once a day.

In the present description, the term "step" not only refers to an independent step, but also includes a step that cannot be clearly distinguished from another step provided the intended objective of that step is achieved. In addition, unless specifically indicated otherwise, the content of each component of a composition refers to the total amount of a plurality of those substances present in the composition in the case a plurality of types of the substances are present for each component in the composition.

The following provides an explanation of embodiments of the present invention.

(1) Pharmaceutical Preparation of Present Invention

The pharmaceutical preparation of the present invention is an agent and/or pharmaceutical for improving human ocular subjective symptoms that contains HA having an aminoalkyl cinnamate covalently bonded thereto (hereinafter referred to as the "present compound").

(1-1) Present Compound

The present compound that is an active ingredient of the pharmaceutical preparation of the present invention is a compound in which an aminoalkyl cinnamate and HA are covalently bonded (hyaluronic acid derivative). Examples of the "aminoalkyl cinnamate" include aminoethyl cinnamate and aminopropyl cinnamate. Among these, 2-aminoethyl cinnamate and 3-aminopropyl cinnamate are preferable, while 3-aminopropyl cinnamate is particularly preferable. In the present description, and including the following explanation, it should be readily understood that the term "aminoalkyl cinnamate" includes and can be interchanged with these specific and/or preferable cinnamic acid esters.

There are no particular limitations on the HA having this "aminoalkyl cinnamate" covalently bonded thereto as far as it is a glycosaminoglycan which contains disaccharide units comprising N-acetyl-D-glucosamine attached to D-glucuronic acid in β1,3-linkage and the disaccharide units are connected each other repeatedly by β1,4-linkage. In addition, it may be in a free state without forming a salt or may be in the form of a pharmaceutically acceptable salt.

Examples of pharmaceutically acceptable salts of HA include alkaline metal ion salts such as sodium salts or potassium salts, alkaline earth metal salts such as magnesium salts or calcium salts, salts of inorganic bases such as ammonium salts, and salts of organic bases such as diethanolamine, dicyclohexylamine or amino acids. The HA salt is preferably a salt formed with an alkaline metal ion and particularly a salt formed with a sodium ion.

The HA may be any of that derived from a natural substance obtained by extracting from a portion of a living organism such as cockscomb, umbilical cord, cartilage or skin, that which has been chemically synthesized, and that which has been produced by microbial culturing or genetic engineering techniques. Furthermore, since the present compound is administered to a living organism, in addition to the present compound per se, the HA serving as the raw material thereof is preferably also of high purity and substantially free of contaminants for which the presence thereof is not acceptable for pharmaceutical use.

There are no particular limitations on the weight-average molecular weight of the HA, and may be, for example, 10,000 to 5,000,000. The weight-average molecular weight of the HA is preferably 200,000 to 3,000,000 and more preferably 500,000 to 2,500,000. Furthermore, the weight-average molecular weight of the HA can be measured by the limiting viscosity method.

The present compound can be produced by covalently bonding this HA with an aminoalkyl cinnamate. There are no particular limitations on the mode of this covalent bonding, and preferably the amino group of the aminoalkyl cinnamate is linked with the carboxyl group of HA through an amide linkage. The following provides an explanation using the present compound in which the covalent bond consists of an amide linkage as an example.

In the present compound, all of the carboxyl groups of HA are not necessarily required to form an amide linkage with the aminoalkyl cinnamate, but rather only a portion of these groups may form an amide linkage. In the subsequent descriptions, the ratio of all carboxyl groups present in HA that form an amide linkage is referred to as the "degree of substitution" (DS). DS is calculated from the ratio (%) of the number of aminoalkyl cinnamate residues introduced per constituent disaccharide unit of HA. For example, the DS of an HA derivative in which one aminoalkyl cinnamate residue is introduced per constituent disaccharide unit is 100%, while the DS of an HA derivative in which one aminoalkyl cinnamate residue is introduced per 200 sugars (100 constituent disaccharide units) is 1%.

The value of DS in the present compound is preferably 3-30%, more preferably 10-20% and even more preferably 12-18%.

The present compound can be produced by linking an amino group derived from an aminoalkanol that composes the aminoalkyl cinnamate (in the manner of, for example, an aminoethanol (such as 2-aminoethanol) or an aminopropanol (such as 3-aminopropanol)) with the carboxyl group of HA.

The aminoalkyl cinnamate is an ester compound in which the carboxyl group of cinnamic acid and the hydroxyl group of the aminoalkanol are bonded through an ester linkage. Furthermore, the cinnamic acid that composes the aminoalkyl cinnamate may be a substituted cinnamic acid having a substituent.

The present compound can be produced in compliance with the method described in, for example, Japanese Patent Application Laid-Open (JP-A) No. 2002-249501 or International Publication No. WO 2008/069348.

There are no particular limitations on the production method provided it allows the aminoalkyl cinnamate and HA to be chemically bonded through an amide linkage. Examples of production methods include a method that uses a water-soluble condensing agent such as a water-soluble carbodiimide (such as 1-ethyl-3-(3-dimethylaminopropyl) carbodiimide hydrochloride (EDCI.HCl) or 1-cyclohexyl-3-(2-morpholinoethyl) carbodiimide-metho-p-toluenesulfonate), a method that uses the aforementioned condensing agent and a condensation assistant such as N-hydroxysuccinimide (HOSu) or N-hydroxybenzotriazole (HOBt), a method that uses a condensing agent such as 4-(4,6-dimethoxy-1,3,5-triazin-2-yl)-4-methylmorpholinium chloride (DMT-MM), an active esterification method and an acid anhydride method.

The present compound may be prepared by preliminarily reacting cinnamic acid with an aminoalkanol (such as 3-aminopropanol, to apply similarly hereinafter) to prepare an aminoalkyl cinnamate (such as 3-aminopropyl cinnamate, to apply similarly hereinafter) followed by allowing the amino group of the aminoalkyl cinnamate to bond with the carboxyl group of HA through an amide linkage, or by allowing the amino group of an aminoalkanol to bond with the carboxyl group of HA through an amide linkage to prepare HA having an aminoalkanol introduced therein, followed by allowing the carboxyl group of cinnamic acid to bond with a hydroxyl group derived from the aminoalkanol present in the aforementioned HA having an aminoalkanol introduced therein through an ester linkage.

(1-2) Formulation

The pharmaceutical preparation of the present invention can be produced by incorporating HA having an aminoalkyl cinnamate covalently bonded thereto and formulating into a preparation. Although there are no particular limitations on the formulation method provided the preparation can be made to be in the form of a preparation and/or pharmaceutical administered to the human eye, it is preferably in the form of a solution. This solution is preferably an ocular solution or ophthalmic solution.

In addition, since the present compound demonstrates a remarkable and/or heterogeneous effect at a concentration of 0.3% (w/v), the pharmaceutical preparation of the present invention is preferably in the form of a solution and contains the present compound at a concentration of 0.3% (w/v) as will be subsequently described.

In the formulation of such a preparation, the addition of a pharmaceutically acceptable carrier as necessary, sterilization of the preparation, and filling into a container suitable for administration to the human eye can be suitably carried out by a person with ordinary skill in the art.

To the pharmaceutical preparation of the present invention, it can be selected and added a buffering agent such as sodium phosphate, sodium hydrogen phosphate, sodium dihydrogen phosphate, sodium acetate or ε-aminocaproic acid, an isotonic agent such as sodium chloride, potassium chloride or concentrated glycerin, a surfactant such as polyoxyethylene sorbitan monooleate, polyoxyl 40 stearate or polyoxyethylene hydrogenated castor oil, or a preservative such as benzalkonium chloride, as necessary.

In addition, although there are no particular limitations on the pH of the pharmaceutical preparation of the present invention within the acceptable range for the ophthalmic preparations, it is preferably within the range of pH 5 to 6.

(1-3) Method of Using Pharmaceutical Preparation of the Present Invention

The pharmaceutical preparation of the present invention can be used by administering to a human eye. Administration of the pharmaceutical preparation of the present invention to a human eye may be carried out by a method that is medically acceptable for administration to a human eye, and there are no particular limitations thereon provided the effects of the present invention can be demonstrated.

There are no particular limitations on the specific administration method, and although the pharmaceutical preparation of the present invention may be suitably administered corresponding to the form of the preparation, a preferable example thereof is instillation.

In addition, although there are no particular limitations on the number of times or frequency of administration of the pharmaceutical preparation of the present invention, preferable examples thereof include administering 1 to 6 times per day, administering about 4 times per day, administering everyday, continuously administering daily for 14 days or longer and continuously administering daily for 28 days or longer, while a combination thereof, (such as administering about 4 times per day every day, continuously administering about 4 times per day for 14 days or more, or continuously administering about 4 times per day for 28 days or more) is more preferable. In addition, examples of the daily dosage include administration of 1, 2 or 3 drops per administration.

Human ocular subjective symptoms can be improved by administering the pharmaceutical preparation of the present invention to a human eye. There are no particular limitations on the person targeted for administration of the pharmaceutical preparation of the present invention provided he or she is a person exhibiting ocular subjective symptoms. In addition, there are no particular limitations on the purpose of administration provided it is for improving human ocular subjective symptoms.

There are no particular limitations on the "ocular subjective symptoms" described in the present description, and examples thereof include ocular discomfort (not including discomfort such as physical irritation caused by administration of a preparation to the eye per se, but including the discomfort normally felt by dry eye patients), dryness (feeling that the eyes are dry), burning (feeling that the eyes are hot and smarting), feeling of a foreign body (strange feeling that something is contacting the eye during blinking or eyes feeling gritty), grittiness (feeling that the surface of the eye is not smooth as if sand had entered the eyes), stinging (painful sensation as if pricked with a needle), bleariness, itchiness, sensitivity to light and blurry vision, and the pharmaceutical preparation of the present invention can be applied to one or two or more of these symptoms.

Since the pharmaceutical preparation of the present invention is particularly effective for one or two or more subjective symptoms selected from the group consisting of ocular discomfort, dryness, burning, grittiness and stinging, among these, for one or two or more subjective symptoms selected from the group consisting of ocular discomfort, dryness, burning and grittiness, and especially for one or two or more subjective symptoms selected from the group consisting of ocular discomfort, dryness and grittiness, the pharmaceutical preparation of the present invention is preferably administered to persons having these symptoms or is preferably administered for the purpose of improving these symptoms.

Since the pharmaceutical preparation of the present invention demonstrates effects that improve subjective symptoms, in particular immediately after the start of administration, and is effective for improving subjective symptoms at an early stage after the start of administration, it is preferably used for the purpose of improving subjective symptoms at an early stage after the start of administration. In the present description, "early stage after the start of administration" refers to a period of several weeks after the start of administration, preferably refers to a period up to and including about day 13, and more preferably refers to a period up to and including about day 6, when defining the day on which administration is started as day 0.

In addition, in the present description, "immediately after the start of administration" refers to the day following the start of administration.

Among human ocular subjective symptoms, ocular discomfort and dryness are the most frequently indicated as chief complaints of dry eye patients, accounting for roughly 80% of all complaints. As a result of improving these subjective symptoms at an early stage after the start of administration, or immediately after the start of administration in particular, dry eye patients are encouraged to continue administration of their own volition, making it possible to reliably demonstrate expected therapeutic effects. As is indicated in the examples to be subsequently described, since the pharmaceutical preparation of the present invention demonstrated efficacy from immediately after the start of administration and at an early stage after the start of administration in analyses of the average values of scores used to evaluate these subjective symptoms, the pharmaceutical preparation of the present invention can be expected to promote voluntary continuation of administration by the patient per se as well as demonstrate therapeutic effects.

In addition, since the pharmaceutical preparation of the present invention is effective for improving the aforementioned subjective symptoms particularly in persons in which these symptoms are felt especially strongly (persons with severe subjective symptoms such as persons exhibiting an average score of 2.5 or higher for the worst subjective symptom), the pharmaceutical preparation of the present invention is administered to such persons for that purpose. As explained in the examples to be subsequently described, the "score" referred to here indicates a score of 0 (no subjective symptoms) to 5 (worst subjective symptoms) used to evaluate each of the aforementioned symptoms in accordance with that perceived by the person administered the pharmaceutical preparation of the present invention. Among scores given for each of the subjective symptoms, those persons having an average of 2.5 or higher for the highest score are considered to be "persons exhibiting an average score of 2.5 or higher for the worst subjective symptom". In addition, a person administered the pharmaceutical preparation of the present invention is preferably a person with dry eye (in the present specification, dry eye has same meaning with dry eye disease and dry eye syndrome).

Since the pharmaceutical preparation of the present invention is particularly effective for improving subjective symptoms before bedtime at which time subjective symptoms are thought to appear with the greatest severity as a result of having used the eyes throughout the day, the pharmaceutical preparation of the present invention can be used for the purpose of improving subjective symptoms before bedtime in this manner.

The term "improvement" of subjective symptoms in the present description refers to a decrease in subjective symptoms. Improvement of subjective symptoms can be evaluated quantitatively by a decrease in the subjective symptoms score.

(2) Method of Present Invention

The method of the present invention is a method for improving human ocular subjective symptoms that comprises a step for administering the present compound (which naturally includes that in the form of the pharmaceutical preparation of the present invention) to the eye of a human. The method of the present invention can be carried out in the same manner as that in accordance with the explanation described in the aforementioned section (1) entitled "Pharmaceutical Preparation of Present Invention". Thus, for example, administration of the present compound preferably being in the form of a 0.3% (w/v) solution and the person receiving administration preferably being a person with dry eye are the same as previously described.

The present invention includes the use of the present compound for improving human ocular subjective symptoms and the use of the pharmaceutical preparation of the present invention for improving human ocular subjective symptoms.

EXAMPLES

The following provides an explanation of the present invention through examples thereof. However, the technical scope of the present invention is not limited thereby.

Example 1

Preparation of HA Having Aminoalkyl Cinnamate Covalently Bonded Thereto

HA having an aminopropyl cinnamate covalently bonded thereto was prepared in compliance with the method described in Example 2 of JP-A 2002-249501 using HA having a weight-average molecular weight of 880,000 (as measured according to the limiting viscosity method). In the following descriptions, this "HA having an aminopropyl cinnamate covalently bonded thereto" is abbreviated as "HA-3APC". As a result of analyzing the resulting HA-3APC according to the method described in the examples of JP-A 2002-249501, the degree of substitution of the aminopropyl cinnamate per HA repeating disaccharide unit was 15.3%.

Example 2

Preparation of Ophthalmic Solution 1

After adding phosphate-buffered saline (PBS) to the HA-3APC (test substance) prepared in Example 1 and preparing solutions containing HA-3APC at 0.5 w/v %, 0.3 w/v % and 0.1 w/v %, the resulting solutions were subjected to filtration sterilization using a 0.22 μm filter to obtain ophthalmic solutions. These ophthalmic solutions are referred to as the 0.5% test compound solution, 0.3% test compound solution and 0.1% test compound solution, respectively.

Reference Example 1

Test Using Animal Dry Eye Disease Model (1) Preparation of Model Animals

Seven-week-old SD male rats (SPF) were mildly anesthetized with diethyl ether following by shaving hair from the cheeks on both the left and right sides under isoflurane inhalation anesthesia.

After disinfecting the shaved areas with 70% ethanol solution, incisions were made at locations about 7 mm below the ears that extended about 7 mm in the longitudinal direction followed by excision of the extraorbital lacrimal glands of both eyes. Next, an antimicrobial agent (Tarivid™ ophthalmic ointment) was applied to the incision wound, and after suturing the wound, the sutured wound was disinfected with 10% povidone-iodine solution.

Two months after excision of the lacrimal glands, the corneal epithelia of both eyes were subjected to fluorescein staining using Fluores™ Test Paper (Showa Yakuhin Kako Co., Ltd.) under isoflurane inhalation anesthesia. As a result, defective areas (damaged areas) of the corneal epithelia were fluorescein-stained.

The entire cornea was macroscopically divided from above into three sections while illuminated with a slit lamp (SL-D7, Topcon Corp.) and the degree of damage to the corneal epithelia was evaluated based on the following criteria for each section (maximum score of 9 per eye). The scores for each animal were indicated as the average of both eyes. In addition, the entire cornea of each animal scored was photographed using a digital photography unit.

(Criteria)

0 points: Absence of stained dots 1 point: Sparse (fluorescein-stained dots are separated from each other)

2 points: Moderate (intermediate to sparse and dense)

3 points: Dense (nearly all fluorescein-stained dots are adjacent to each other)

(2) Grouping

The model animals prepared in the manner described above were divided into the 9 groups shown in Table 1 after scoring so that the average scores were the same among the groups.

TABLE 1

| Group | Administered Substance | Number of Animals (Eyes) | Dosage per administration | Dosing frequency (times/day) |
|---|---|---|---|---|
| Control group (once per day) | PBS | 5 (10) | 5 µL | 1 time |
| Control group (6 times per day) | PBS | 5 (10) | 5 µL | 6 times |
| 0.1% group (once per day) | 0.1% test substance solution | 5 (10) | 5 µL | 1 time |
| 0.3% group (once per day) | 0.3% test substance solution | 5 (10) | 5 µL | 1 time |
| 0.5% group (once per day) | 0.5% test substance solution | 5 (10) | 5 µL | 1 time |
| 0.1% group (6 times per day) | 0.1% test substance solution | 5 (10) | 5 µL | 6 times |
| 0.3% group (6 times per day) | 0.3% test substance solution | 5 (10) | 5 µL | 6 times |
| 0.5% group (6 times per day) | 0.5% test substance solution | 5 (10) | 5 µL | 6 times |
| Normal group | None | 3 (6) | None | None |

(3) Test Method

The test substance was administered to each group in accordance with Table 1. The test substance was administered by instillation using a continuous dispenser (Multipette Plus, Eppendorf Co.). Furthermore, those groups that were dosed 6 times per day were dosed a total of 6 times at 1.5 hour intervals, those groups dosed once per day were dosed once per day at the time of the initial dosing of the groups dosed 6 times per day, and this was continued for 21 days (3 weeks). The degree of damage to corneal epithelia was evaluated immediately after the start of administration (day 0), on day 3 and at the days after 1 week, 2 weeks and 3 weeks. Damage was evaluated in accordance with the aforementioned criteria and scored under blind conditions.

The results for each group were indicated as the mean±standard error. The scores for each group dosed with a test substance solution at each evaluation time were confirmed for dose response according to the Shirley-Williams test and Jonckheere-Terpstra test. A level of significance of less than 5% was considered to be significant.

(4) Test Results

Figure 2:
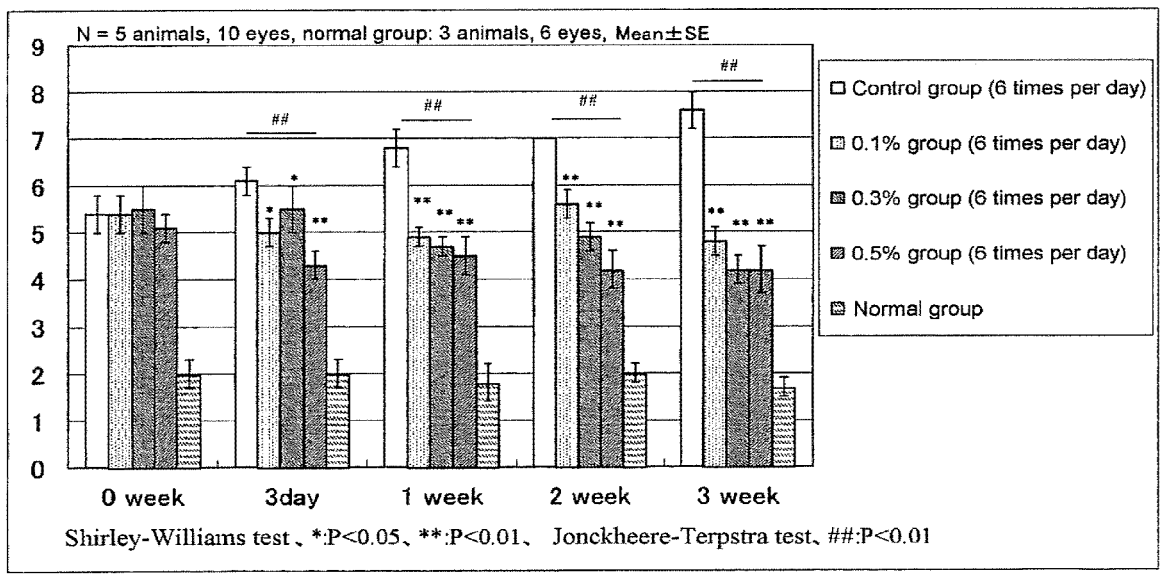
FIG. 2 indicates the degree of fluorescein staining in the case of having administered a preparation to the eye of a model animal six times a day.

The results are shown in FIGS. 1 and 2. According to the results of the dose-response relationship test as determined according to the Shirley-Williams test, among those groups dosed once per day (FIG. 1), significant differences were observed versus the control group (once per day) for the group dosed at 0.5% at all evaluation times after day 3 and for the groups dosed at 0.1% and 0.3% at the days after the 1 week and 3 weeks. In addition, among those groups dosed 6 times per day (FIG. 2), significant differences were observed versus the control group (6 times per day) for all groups dosed with the test substance at all evaluation times after day 3.

In addition, according to the results of the dose-response trend test as determined according to the Jonckheere-Terpstra test, among those groups dosed once per day (FIG. 1), the Jonckherre statistic was significant on day 3 and at the days after the 2 week and 3 weeks, and among those groups dosed 6 times per day (FIG. 2), the Jonckherre statistic was significant at all evaluation times.

Since dosing once per day and dosing 6 times per day were significant for both tests at the time of the final evaluation at the day after the 3 weeks, a dose-response relationship was indicated regardless of the administration frequency per day.

Example 3

Preparation of Ophthalmic Solution 2

A base (consisting of sodium chloride and potassium chloride as isotonic agents, sodium hydrogen phosphate and sodium dihydrogen phosphate as buffering agents, disodium edetate as stabilizer, and 0.003% benzalkonium chloride as preservative) was added to the HA-3APC prepared in Example 1, and after adjusting the pH to 5.0 to 6.0 to prepare 0.5 w/v % and 3.0 w/v % HA-3APC solutions, the solutions were subjected to filtration sterilization with a 0.22 µm filter to obtain ophthalmic solutions. These solutions are referred to as a 0.5% ophthalmic solution and 0.3% ophthalmic solution, respectively. In addition, a base solution not containing HA-3APC was prepared for use as a placebo.

Example 4

Clinical Study in Dry Eye Patients Using CAE™ Model (1) Subjects

Dry eye patients who satisfied all of the following conditions of A) to C) were enrolled in the study:

A) Age 18 or older,

B) Provided written informed consent, and

C) History of dry eye in both eyes.

However, dry eye patients applicable to any of the following a) to d) were excluded from the study:

a) Wear contact lenses, b) Have an uncontrollable systemic disease, c) Have an uncontrollable mental disease, drug addiction or alcohol addiction, and d) Lactating or pregnant women and women planning to become pregnant.

(2) Study Method

A joint multicenter, randomized, double-blind comparative study was conducted using a CAE™ (Controlled Adverse Environment) model (Ora, Inc., Andover, Mass., USA) (refer to George W. Ouster, et al., Ann Allergy Asthma Immunol, 2004; 93: 460-464), which has been established to evaluate the therapeutic effects of the treatments for dry eye in the field of ophthalmology, in which the humidity kept low, temperature, air flow, lighting conditions and visual tasking were controlled.

First, as an introduction to the study, the subjects dropped a placebo into both eyes at 1 drop per administration 4 times per day (morning, noon, afternoon and before bedtime), and this was continued for 2 weeks as a run-in period. The subjects were instructed to score ocular subjective symptoms (ocular discomfort, dryness, burning, grittiness and stinging) based on their own perception of those symptoms and record them in a daily diary at bedtime (prior to instillation before bedtime) every day during the run-in period. The scores ranged from 0 (absence of subjective symptoms) to 5 (most severe (worst) subjective symptoms).

(3) Administration of Ophthalmic Solutions

Next, the subjects dropped in the 0.5% ophthalmic solution or 0.3% ophthalmic solution prepared in Example 3 or the placebo in both eyes at 1 drop per administration 4 times per day (morning, noon, afternoon and before bedtime), and this was continued for 4 weeks. The subjects were instructed to score subjective symptoms and record them in a daily diary at bedtime (prior to instillation before bedtime) every day during the instillation period.

(4) Results

Subjects who strongly perceived subjective symptoms (subjects having an average score of 2.5 or higher for the most severe (highest) subjective symptom score (worst symptom score)) immediately before starting administration of ophthalmic solution (period of 7 days to 1 day before the start of administration of ophthalmic solution) were evaluated, and their time-based changes during the administration period were graphed.

Differences from the average subjective symptom score immediately before instillation performed on day 0 (period of 7 days to 1 day before the start of administration of ophthalmic solution) in each dose group (baseline) were used for evaluation. In addition, the average score for each subjective symptom in each dose group at each evaluation time was used for this evaluation. The results are shown in FIGS. 3 to 8.

Furthermore, since these results indicate results obtained at bedtime (prior to instillation before bedtime) when eye fatigue had accumulated following continuous use of the eyes throughout the day, they are considered to represent the strongest appearance of subjective symptoms while also having a considerable effect on sleep. Namely, the following results were obtained by evaluating those patients presenting with severe subjective symptoms at a time of the day when the symptoms are thought to appear most intensely.

Furthermore, the number of subjects in the 0.5% ophthalmic solution, 0.3% ophthalmic solution and placebo groups were 23, 26 and 26, respectively.

(4-1) Ocular Discomfort

Figure 3:
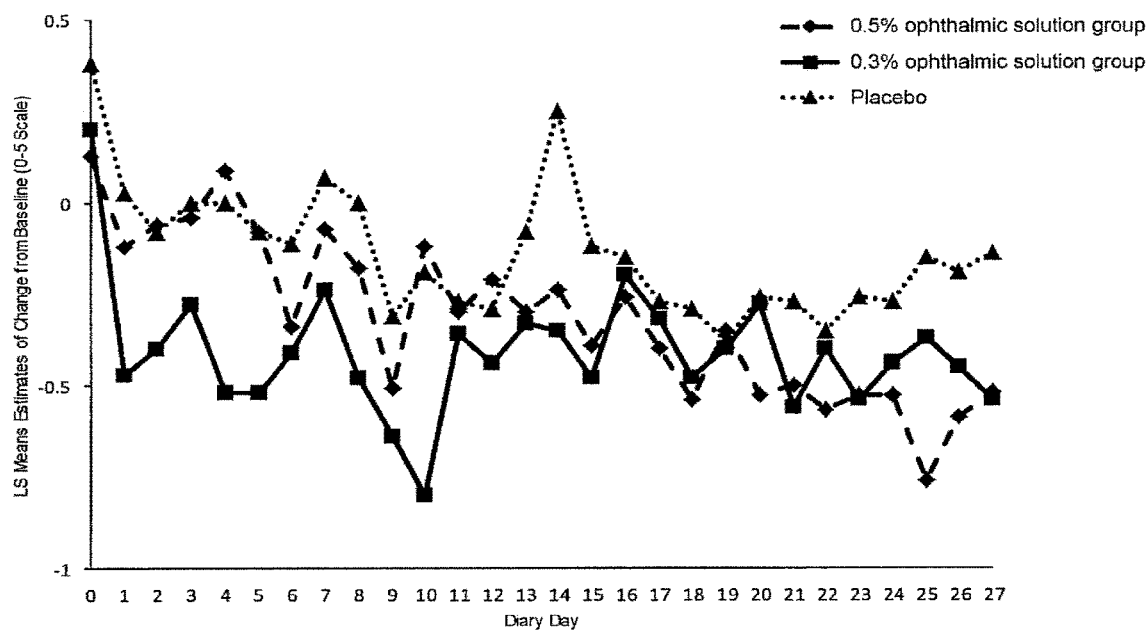
FIG. 3 indicates changes in a subjective symptom (ocular discomfort) in the case of having administered a preparation to the eye of a human patient.

Results for ocular discomfort are shown in FIG. 3. As a result of analyzing these results, statistically significant decreases in subjective symptoms versus the placebo group were observed in the 0.3% ophthalmic solution group during the time periods indicated below.

Day 0 to Day 6 (P=0.0219, t-test; P=0.0249, ANCOVA)
Day 0 to Day 13 (P=0.0143, t-test; P=0.0210, ANCOVA)
Day 0 to Day 20 (P=0.0387, t-test)
Day 7 to Day 13 (P=0.0233, t-test; P=0.0407, ANCOVA)

On the other hand, a statistically significant difference versus the placebo group was observed in the 0.5% ophthalmic solution group only during the period from Day 21 to Day 27 (P=0.0306, test method: t-test).

In this manner, these results surprisingly showed that the 0.3% ophthalmic solution demonstrated an ameliorative effect on human ocular subjective symptoms (ocular discomfort) at an early stage after the start of administration of ophthalmic solution (Day 0 to Day 20), and that the effect was superior to that of the 0.5% ophthalmic solution.

(4-2) Dryness

Figure 4:
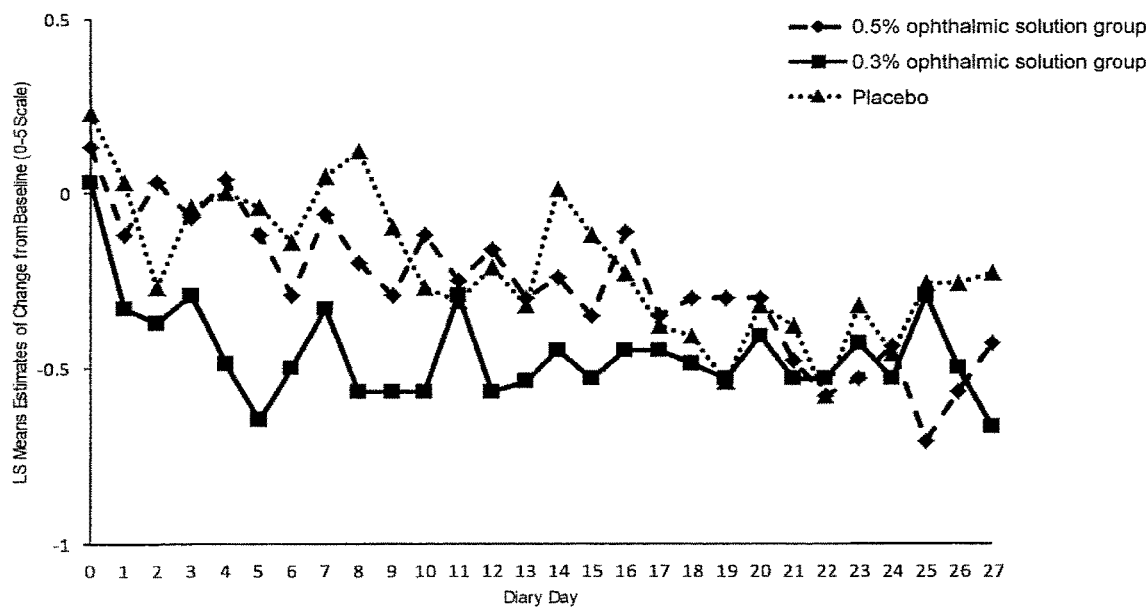
FIG. 4 indicates changes in a subjective symptom (dryness) in the case of having administered a preparation to the eye of a human patient.

The results for dryness are shown in FIG. 4. As a result of analyzing these results, statistically significant decreases in subjective symptoms versus the placebo group were observed in the 0.3% ophthalmic solution group during the time periods indicated below.

Day 0 to Day 6 (P=0.0480, t-test)
Day 0 to Day 13 (P=0.0173, t-test; P=0.0259, ANCOVA)
Day 0 to Day 20 (P=0.0466, t-test)
Day 7 to Day 13 (P=0.0140, t-test; P=0.0240, ANCOVA)
Day 0 to Day 27 (P=0.0365, Wilcoxon rank stun)

On the other hand, statistically significant differences were not observed in the 0.5% ophthalmic solution group.

In this manner, these results surprisingly showed that the 0.3% ophthalmic solution demonstrated an ameliorative effect on human ocular subjective symptoms (dryness) at an early stage after the start of administration of ophthalmic solution (Day 0 to Day 27), and that the effect was superior to that of the 0.5% ophthalmic solution.

(4-3) Grittiness

Figure 5:
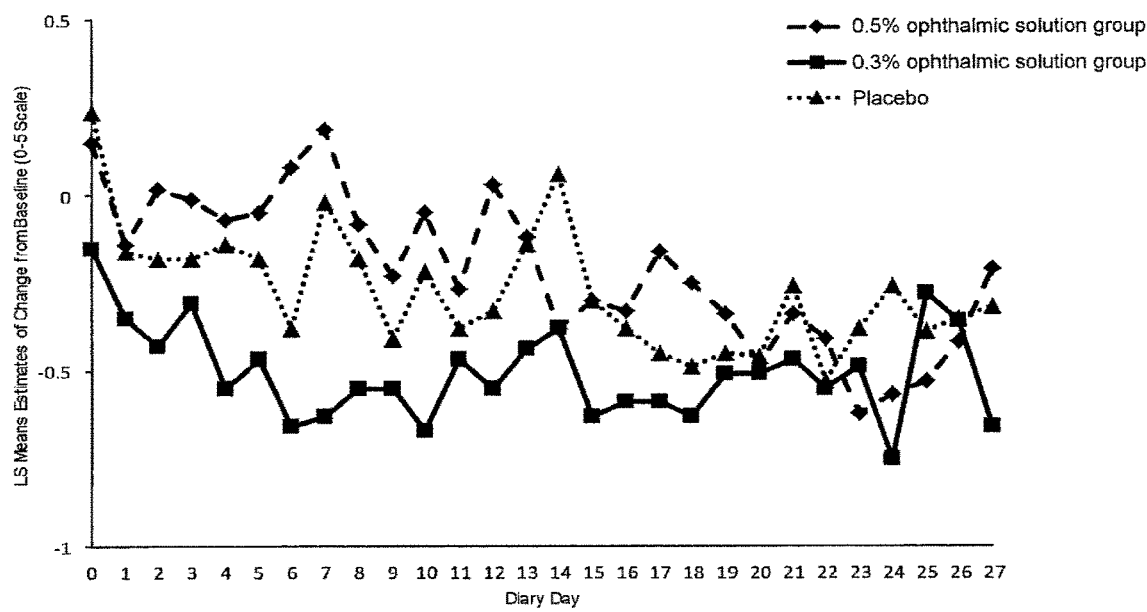
FIG. 5 indicates changes in a subjective symptom (grittiness) in the case of having administered a preparation to the eye of a human patient.

The results for grittiness are shown in FIG. 5. As a result of analyzing these results, a statistically significant decrease in subjective symptoms versus the placebo group was observed in the 0.3% ophthalmic solution group during the time period from day 0 to day 13 (P=0.0286, Wilcoxon rank sum).

On the other hand, statistically significant differences were not observed in the 0.5% ophthalmic solution group.

In this manner, these results surprisingly showed that the 0.3% ophthalmic solution demonstrated an ameliorative effect on human ocular subjective symptoms (grittiness) at an early stage after the start of administration of ophthalmic solution (Day 0 to Day 13), and that the effect was superior to that of the 0.5% ophthalmic solution.

(4-4) Worst Subjective Symptom Score

Figure 6:
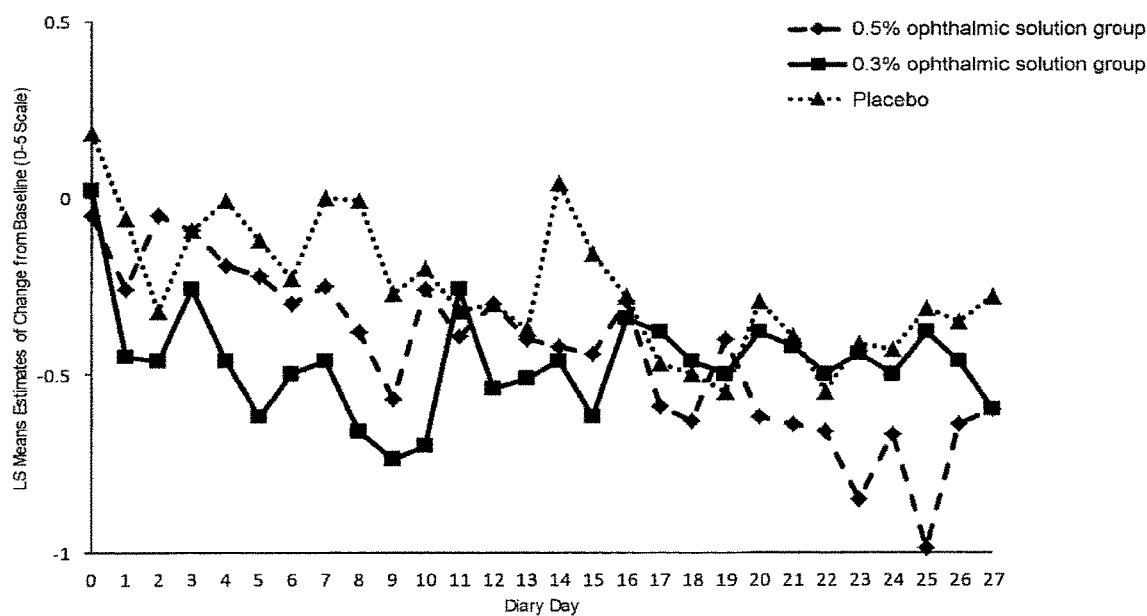
FIG. 6 indicates changes in the worst of various subjective symptoms in the case of having administered a preparation to the eye of a human patient.

FIG. 6 indicates the results for the subjective symptom perceived by each patient (ocular discomfort, burning, dryness, grittiness and stinging) to be the worst subjective symptom (highest symptom score).

As a result of analyzing these results, statistically significant decreases in subjective symptoms versus the placebo group were observed in the 0.3% ophthalmic solution group during the time periods indicated below.

Day 0 to Day 13 (P=0.0232, t-test; P=0.0324, ANCOVA)
Day 7 to Day 13 (P=0.0204, t-test; P=0.0308, ANCOVA)

On the other hand, statistically significant differences were not observed in the 0.5% ophthalmic solution group.

In this manner, these results surprisingly showed that the 0.3% ophthalmic solution demonstrated an ameliorative effect on the worst human ocular subjective symptoms at an early stage after the start of administration of ophthalmic solution (Day 0 to Day 13), and that the effect was superior to that of the 0.5% ophthalmic solution.

(4-5) Average of Subjective Symptom Score

Figure 7:
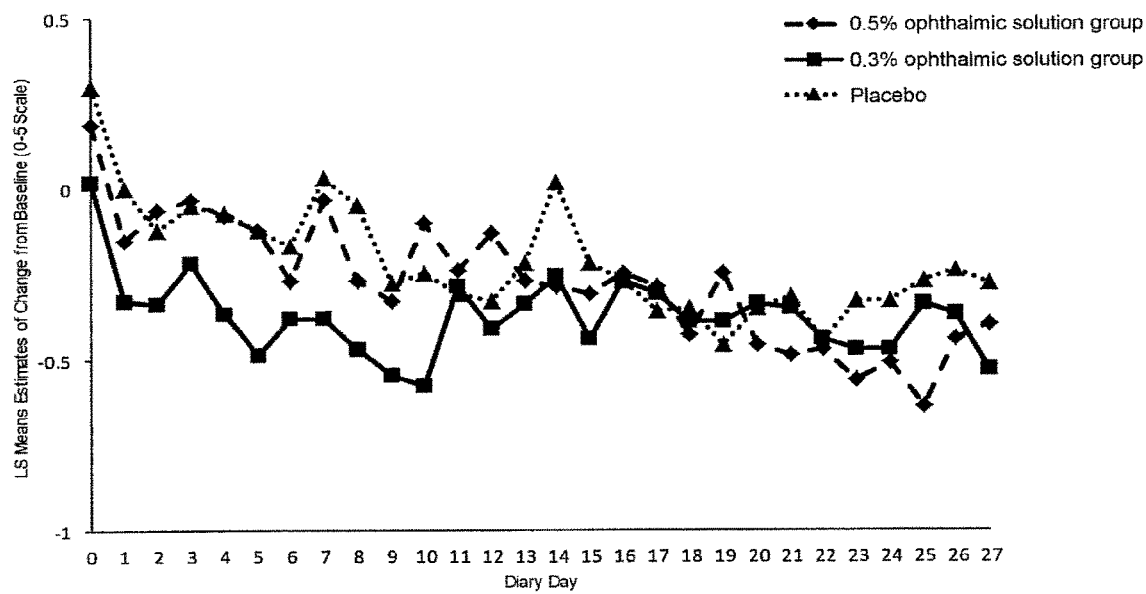
FIG. 7 indicates changes in the average value of all subjective symptoms in the case of having administered a preparation to the eye of a human patient.

FIG. 7 indicates the results of analyzing the average score of each patient for each subjective symptom (ocular discomfort, dryness, burning, grittiness and stinging).

Statistically significant decreases in subjective symptoms versus the placebo group were observed in the 0.3% ophthalmic solution group during the time periods indicated below.

Day 0 to Day 6 (P=0.0481, t-test)
Day 0 to Day 13 (P=0.0404, t-test; P=0.0422, ANCOVA)
Day 7 to Day 13 (P=0.0148, Wilcoxon rank sum)

On the other hand, statistically significant differences were not observed in the 0.5% ophthalmic solution group.

In this manner, these results surprisingly showed that the 0.3% ophthalmic solution demonstrated an ameliorative effect across the entire spectrum of human ocular subjective symptoms at an early stage after the start of administration of ophthalmic solution (Day 0 to Day 6), and that the effect was superior to that of the 0.5% ophthalmic solution.

(4-6) Average of Subjective Symptom Score (Ocular Discomfort, Dryness)

Figure 8:
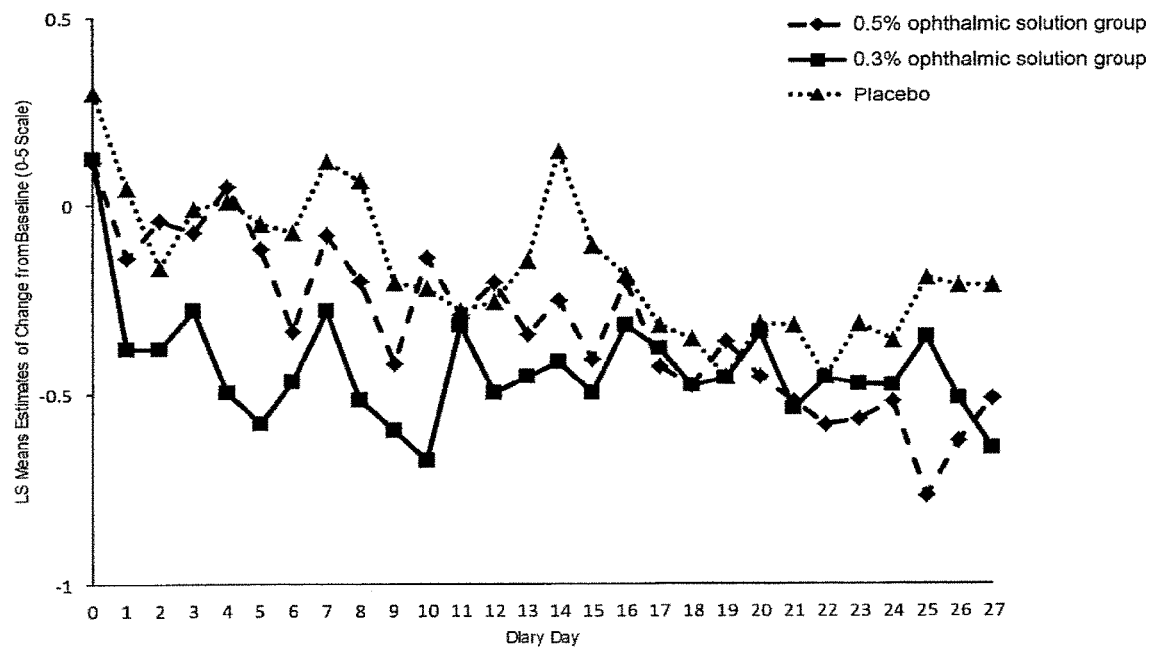
FIG. 8 indicates changes in the average value of subjective symptoms (ocular discomfort and dryness) in the case of having administered a preparation to the eye of a human patient.

FIG. 8 indicates the results of analyzing the average score of each patient for each subjective symptom (ocular discomfort and dryness).

Statistically significant decreases in these subjective symptoms versus the placebo group were observed in the 0.3% ophthalmic solution group during the time periods indicated below.

Day 0 to Day 13 (P=0.0111, t-test; P=0.0080, Wilcoxon rank sum; P=0.0138, ANCOVA)

Days 1, 4, 5, 8, 9 and 10 (P=0.0235, 0.0066, 0.0046, 0.0018, 0.0313 and 0.0145, respectively, t-test)

On the other hand, statistically significant differences were not observed in the 0.5% ophthalmic solution group.

In this manner, these results surprisingly showed that the 0.3% ophthalmic solution demonstrated an ameliorative effect on the human ocular subjective symptoms of ocular discomfort and dryness, for which complaints from patients are the most numerous, at an early stage after the start of administration of ophthalmic solution (and surprisingly, on the day following the start of administration of ophthalmic solution), and that the effect was superior to that of the 0.5% ophthalmic solution.

(5) Changes in Fluorescein Staining Scores Before and After CAE™

Figure 9:
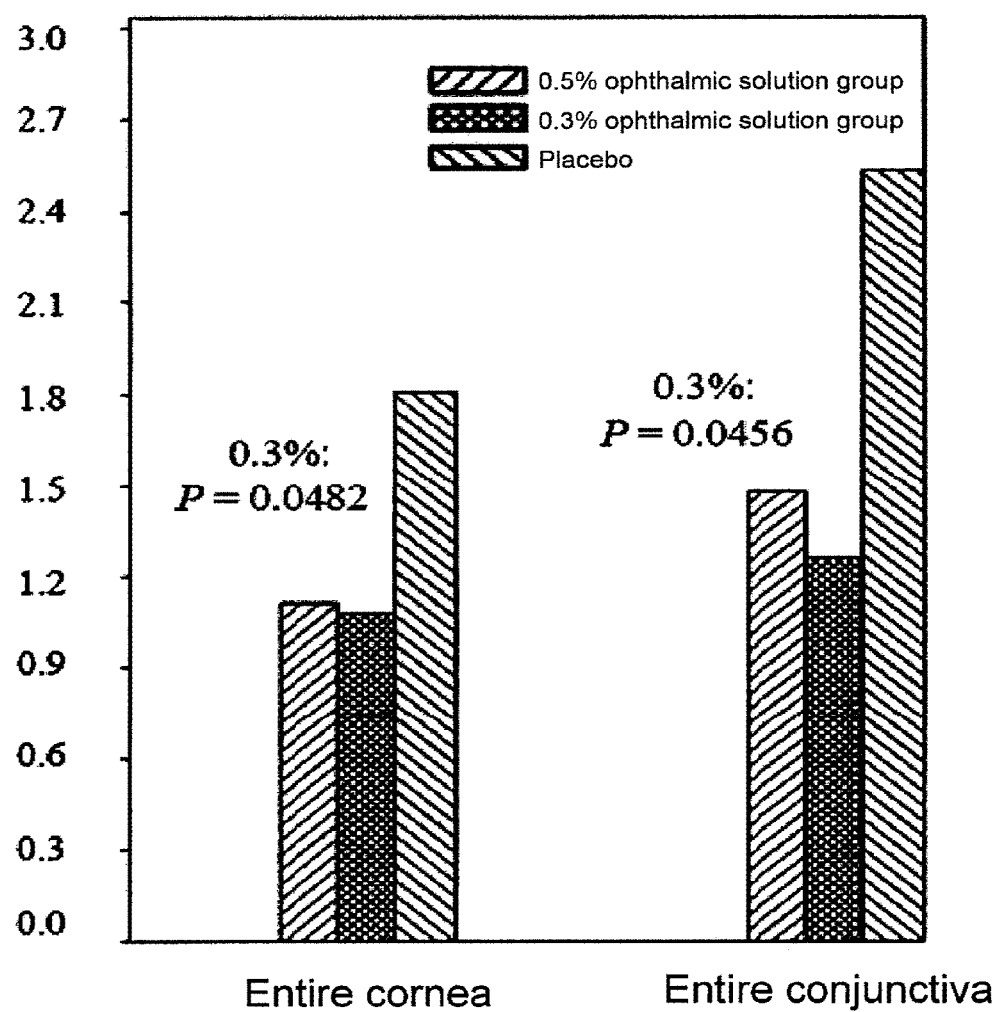
FIG. 9 indicates the degree of fluorescein staining in the case of having administered a preparation to the eye of a human patient.

Changes in fluorescein staining (staining of damaged areas of corneal and conjunctival epithelia) scores for the entire cornea and entire conjunctiva before and after CAE™ were evaluated for each subject on day 28. The results are shown in FIG. 9.

As a result of analyzing the results, statistically significant decreases in staining scores versus the placebo group were observed throughout the entire cornea and conjunctiva in the 0.3% ophthalmic solution group.

On the other hand, there were no statistically significant differences in the 0.5% ophthalmic solution group for either the entire cornea or entire conjunctiva.

In this manner, these results surprisingly showed that the 0.3% ophthalmic solution demonstrated an effect that brought about a decrease in the occurrence of damage to corneal and conjunctival epithelia in human eyes, and that the effect was superior to that of the 0.5% ophthalmic solution.

(6) Evaluation of Safety

There were no statistically significant differences observed among the 0.3% ophthalmic solution group, 0.5% ophthalmic solution group and placebo group with respect to the incidence of systemic adverse events, the incidence of ocular adverse events or the incidence of adverse side effects, and there were no events observed that warranted concern over the safety of HA-3APC.

Disclosures of Japanese Patent Application No. 2001-385072 (filing date: Dec. 18, 2001), Japanese Patent Application No. 2008-519554 (filing date: Oct. 12, 2006), and Japanese Patent Application No. 2014-263710 (filing date: Dec. 26, 2014) are incorporated in the presence description in their entirety by reference.

All publications, patent applications and technical standards described in the present description are incorporated herein by reference to the same extent as if each publication, patent application or technical standard was specifically and individually indicated to be incorporated by reference.

INDUSTRIAL APPLICABILITY

The pharmaceutical preparation of the present invention can be applied industrially as a preparation for improving human ocular subjective symptoms, while the method of the present invention can be applied industrially as a method for improving human ocular subjective symptoms that uses an HA-based compound.

The invention claimed is:

1. An ophthalmic solution, comprising a hyaluronic acid derivative or a pharmaceutically acceptable salt thereof in a concentration of 0.3% (w/v) as an active ingredient,
    wherein the hyaluronic acid derivative is a compound in which an amino group of 3-aminopropyl cinnamate is linked with a carboxyl group of hyaluronic acid through an amide linkage,
    wherein the ophthalmic solution is a pharmaceutical preparation, and
    wherein a pH of the ophthalmic solution is within the range of not less than 5 and not more than 6.

2. The ophthalmic solution according to claim 1, wherein the pharmaceutically acceptable salt is sodium salt.

3. The ophthalmic solution according to claim 1, which further comprises a buffering agent and an isotonic agent.

4. A method for treating dry eye, comprising administering to a dry eye patient an ophthalmic solution according to claim 1.

5. The method according to claim 4, wherein the method is for treating an ocular subjective symptom of dry eye.

6. The method according to claim 5, wherein the method is for further treating an objective sign of dry eye.

7. The method according to claim 4, wherein the ophthalmic solution is administered 1 to 4 times per day.

8. The method according to claim 4, wherein the ophthalmic solution is administered 1, 2 or 3 drops per administration.

* * * * *

UNITED STATES PATENT AND TRADEMARK OFFICE
CERTIFICATE OF CORRECTION

PATENT NO. : 11,779,593 B2
APPLICATION NO. : 17/509576
DATED : October 10, 2023
INVENTOR(S) : Masamichi Yamada et al.

It is certified that error appears in the above-identified patent and that said Letters Patent is hereby corrected as shown below:

On the Title Page

Column 2, Item (56), in "OTHER PUBLICATIONS," Line 1, delete "Ophthamology," and insert -- Ophthalmology, --, therefor.

Column 2, Item (56), in "OTHER PUBLICATIONS," Line 3, delete "Ophthamology," and insert -- Ophthalmology, --, therefor.

Column 2, Item (56), in "OTHER PUBLICATIONS," Line 39, delete "Hylein(R)" and insert -- Hyalein(R) --, therefor.

Column 2, Item (56), in "OTHER PUBLICATIONS," Line 41, delete "Hylein(R)" and insert -- Hyalein(R) --, therefor.

Signed and Sealed this
Twenty-eighth Day of May, 2024

Katherine Kelly Vidal
*Director of the United States Patent and Trademark Office*